United States Patent
Thomas et al.

(10) Patent No.: US 9,931,484 B2
(45) Date of Patent: Apr. 3, 2018

(54) INTERFACE APPLIANCE CARRYING ONE OR MORE SENSORS DETECTING PARAMETERS RELATED TO A FLOW OF FLUID DELIVERED THROUGH THE APPLIANCE

(75) Inventors: Charles Thomas, Monroeville, PA (US); David Harrell, Seattle, WA (US); Stephen Dalton Pittman, Brookline, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 835 days.

(21) Appl. No.: 13/319,113

(22) PCT Filed: May 11, 2010
(Under 37 CFR 1.47)

(86) PCT No.: PCT/IB2010/052095
§ 371 (c)(1),
(2), (4) Date: Nov. 7, 2011

(87) PCT Pub. No.: WO2010/143087
PCT Pub. Date: Dec. 16, 2010

(65) Prior Publication Data
US 2012/0272963 A1    Nov. 1, 2012

Related U.S. Application Data (60) Provisional application No. 61/185,287, filed on Jun. 9, 2009.

(51) Int. Cl.
*A61M 16/00* (2006.01)
*A61M 16/06* (2006.01)

(52) U.S. Cl.
CPC .... *A61M 16/0666* (2013.01); *A61M 16/0009* (2014.02); *A61M 2016/0036* (2013.01);
(Continued)

(58) Field of Classification Search
CPC .......... A61M 16/00; A61M 2016/0036; A61M 2016/0021; A61M 16/0039;
(Continued)

(56) References Cited

U.S. PATENT DOCUMENTS 6,017,315 A * 1/2000 Starr et al. ................... 600/538
6,165,133 A * 12/2000 Rapoport et al. ............. 600/529
(Continued)

FOREIGN PATENT DOCUMENTS

| CN | 101365509 A | 2/2009 |
| JP | 2000500379 A | 1/2000 |
| JP | 2007518480 A | 7/2007 |

*Primary Examiner* — (Jackie) Tan-Uyen T Ho
*Assistant Examiner* — Ned T Heffner
(74) *Attorney, Agent, or Firm* — Michael W. Haas (57) ABSTRACT

An interface appliance is configured to deliver a flow of fluid to the airway of a subject. The generation of the flow of fluid may be controlled to provide a therapeutic benefit to the subject. The interface appliance is configured to carry one or more sensors (24) configured to detect one or more parameters related to the flow of fluid on the subject. The one or more parameters may then be used to control the generation and/or delivery of the flow of fluid.

21 Claims, 5 Drawing Sheets

(52) U.S. Cl.
CPC ........... *A61M 2205/3313* (2013.01); *A61M 2205/3569* (2013.01); *A61M 2205/3592* (2013.01); *A61M 2205/50* (2013.01); *A61M 2230/205* (2013.01)

(58) Field of Classification Search
CPC .... A61M 2016/0027; A61M 2016/003; A61M 2025/0002; A61B 5/00; A61B 5/0017; A61B 5/0075
USPC ............ 128/200.24, 200.26, 203.22, 206.11, 128/207.13, 207.18
See application file for complete search history.

(56) References Cited

U.S. PATENT DOCUMENTS

| | | |
|---|---|---|
| 2007/0027375 A1* | 2/2007 | Melker et al. ............... 600/340 |
| 2007/0107737 A1 | 5/2007 | Landis et al. |
| 2007/0175473 A1 | 8/2007 | Lewis et al. |
| 2008/0051674 A1 | 2/2008 | Davenport et al. |
| 2008/0058621 A1 | 3/2008 | Melker et al. |
| 2008/0142019 A1 | 6/2008 | Lewis et al. |
| 2008/0190436 A1* | 8/2008 | Jaffe et al. ............... 128/207.18 |

\* cited by examiner

INTERFACE APPLIANCE CARRYING ONE OR MORE SENSORS DETECTING PARAMETERS RELATED TO A FLOW OF FLUID DELIVERED THROUGH THE APPLIANCE

The invention relates to the provision of sensors on a nasal cannula that generate one or more output signals that can be used to control the generation of a flow of fluid that is delivered by the nasal cannula.

Nasal cannula for delivering a flow of fluid to the airway of a subject are known. Generally, these nasal cannula are relatively inert devices that provide nothing more than a delivery appliance for delivering the gas to the airway of the patient. Nasal cannula are typically disposable.

One aspect of the invention relates to a system configured to measure one or more parameters. In one embodiment, the system comprises a nasal cannula and one or more sensors. The nasal cannula comprises a main conduit and a pair of hollow prongs that extend from the main conduit. The hollow prongs are configured to be inserted into the nostrils of a subject such that a flow of fluid in the main conduit is communicated to the nostrils of the subject through the hollow prongs. The one or more sensors are carried by the nasal cannula such that at least a portion of each of the one or more sensors are disposed on or directly adjacent to at least one of the hollow prongs. The one or more sensors are configured to generate one or more output signals that convey information related to at least one parameter related to the flow of fluid between the nostrils of the subject and the nasal cannula.

Another aspect of the invention relates to a method of determining a parameter. In one embodiment, the method comprises communicating a flow of fluid with the nostrils of a subject through a nasal cannula comprising a pair of hollow prongs configured to be inserted into the nostrils of a subject; and generating one or more output signals that convey information related to at least one parameter related to the flow of fluid between the nostrils of the subject and the nasal cannula, wherein the one or more output signals are generated by one or more sensors carried by the nasal cannula such that at least a portion of each of the one or more sensors are disposed on or directly adjacent to at least one of the hollow prongs.

Another aspect of the invention relates to a system configured to determine a parameter. In one embodiment, the system comprises means for communicating a flow of fluid with the nostrils of a subject, the means for delivering comprising a pair of hollow prongs configured to be inserted into the nostrils of a subject; and means for generating one or more output signals that convey information related to at least one subject parameter related to the flow of fluid between the nostrils of the subject and the means for delivering, wherein means for generating the one or more output signals are carried by the means for delivering such that at least a portion of each of the means for generating the one or more output signals are disposed on or directly adjacent to at least one of the hollow prongs.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
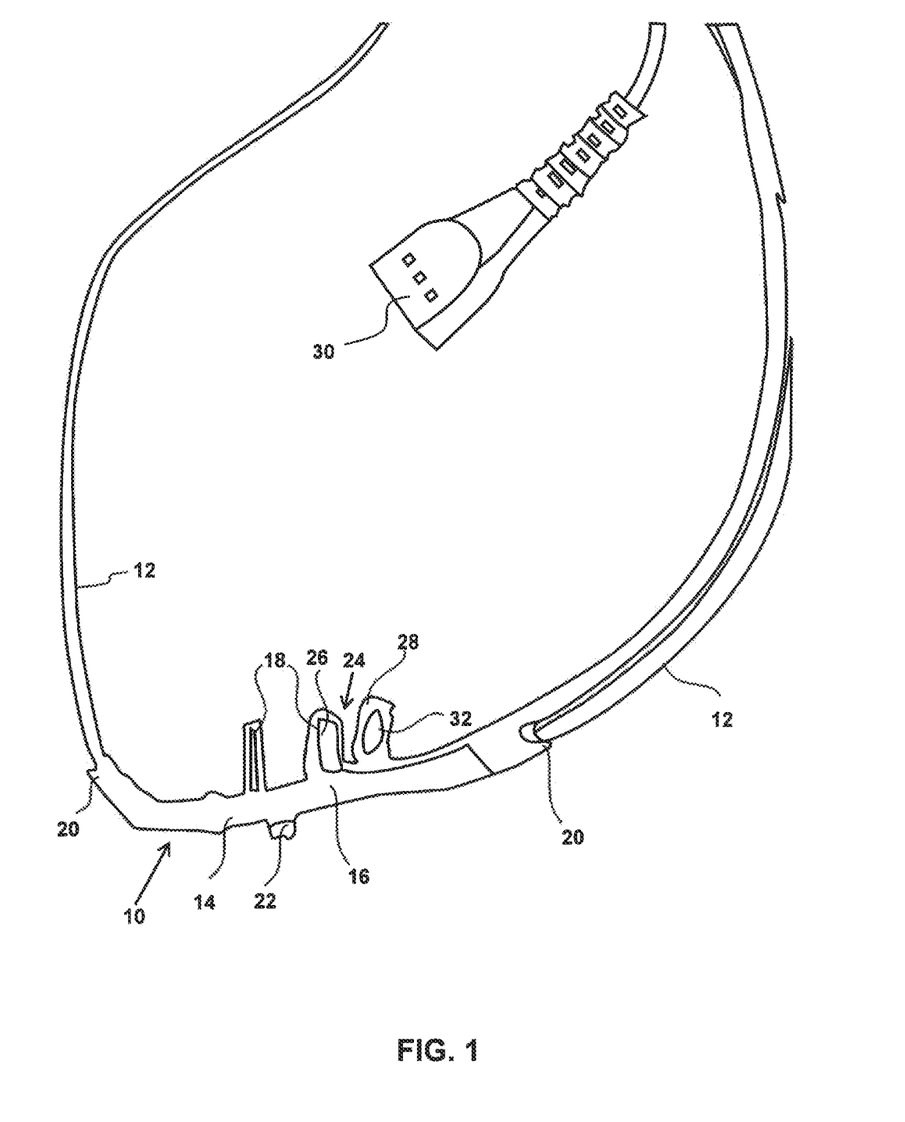
FIG. 1 illustrates an interface appliance configured to deliver a flow of fluid to the airway of a subject, in accordance with one or more embodiments of the invention.

FIG. 1 illustrates an interface appliance 10 configured to communicate a flow of fluid with the airway of a subject. One or more parameters of the flow of fluid may be controlled to provide a therapeutic benefit to the subject. For example, the composition of the flow of fluid may be controlled (e.g., oxygen-enriched), and/or to provide other therapeutic benefits. The interface appliance 10 is configured to carry one or more sensors configured to detect one or more parameters related to the flow of fluid on the subject. The one or more parameters may then be used to control the one or more parameters of the flow of fluid (e.g., as described further below). The interface appliance 10 may include one or more supply line 12, a nasal cannula 14, and/or other components.

The supply lines 12 are configured to carry the flow of fluid to nasal cannula 14. In one embodiment, supply lines 12 are formed separately from nasal cannula 14. In one embodiment, supply lines 12 are not formed as separate components from nasal cannula 14, but instead are integrally formed with nasal cannula 14. When interface appliance 10 is installed on the face of a subject for use, supply lines 12 are typically positioned to run behind the ears of the subject to hold interface appliance 10 in place.

Nasal cannula 14 is configured to communicate the flow of fluid with the nostrils of the subject. This includes passing gas in the flow of fluid to the nostrils during inhalation, and receiving inhaled gas from the nostrils during exhalation. In one embodiment, nasal cannula 14 includes a primary conduit 16, and two hollow prongs 18.

The primary conduit 16 is configured to receive the flow of fluid from supply lines 12, and to communicate the flow of fluid with hollow prongs 16. In the illustrated embodiment, the primary conduit 16 also receives gas exhaled into hollow prongs 18, and conveys the exhaled gas away from the nostrils. As such, primary conduit 16 forms a lumen through which fluid can pass between hollow prongs 16 and supply lines 12. At each end 20 of primary conduit 16, primary conduit 16 is configured to connect to one of supply lines 12 such that the lumen formed within primary conduit 16 is placed in fluid communication with supply lines 12. When nasal cannula 14 is installed on the face of a subject for use, primary conduit 16 rests on or near the face of the subject between the nose and the upper lip.

The primary conduit 16 may include an interface 22 through which a secondary conduit (not shown) may be placed in fluid communication with the lumen formed by primary conduit 16. The secondary conduit may run from interface 22 to the mouth of the subject. If primary conduit 16 is being used without the secondary conduit, interface 22 may be sealed (or substantially sealed) to ambient atmosphere by a plug or seal (not shown).

The hollow prongs 18 are configured to be inserted into the nostrils of the subject when nasal cannula 14 is installed on the face of the subject for use. The hollow prong 18 form lumens that deliver the flow of fluid from the lumen inside primary conduit 16 to and from the nostrils of the subject.

The one or more sensors carried by the interface appliance 10 are configured to generate one or more output signals that convey information related to at least parameter related to the flow of fluid. These parameters may include, for example, one or more physiological parameters of the subject receiving the flow of fluid, one or more gas parameters at or near the point of delivery to the subject, and/or other parameters. By way of non-limiting example, a parameter may include a pulse oximetry parameter that quantifies the oxygenation of the blood within the subject. As another example, a gas parameter may include pressure, flow rate, and/or other gas parameters.

In the embodiment illustrated in FIG. 1, the one or more sensors carried by interface appliance 10 include a pulse oximeter 24. Pulse oximeter 24 is configured to generate one or more output signals that convey information related to the oxygenation of the blood within the subject. The pulse oximeter 24 includes an electromagnetic radiation source 26 and a photosensitive detector 28. The electromagnetic radiation source 26 is carried on interface appliance 10 at or near hollow prong 18. The photosensitive detector 28 is carried on interface appliance 10 such that electromagnetic radiation source 26 and photosensitive detector 28 are substantially equidistant from primary conduit 16 (though spaced apart from each other). For example, interface appliance 10 may include a protrusion 32 that extends from primary conduit 16 to support photosensitive detector 28. The one or more output signals generated by pulse oximeter 24 are output from interface appliance 10 via an electronic interface 30. Power may be received to one or more components of pulse oximeter 24 via electronic interface 28.

In one embodiment (not shown), electronic interface 30 may include one or more wireless transmitter/receivers to communicate an external processor. For example, the output signal(s) may be communicated over the wireless transmitter/receivers.

In one embodiment (not shown), components of interface appliance 10 (e.g., pulse oximeter 24 and/or other sensors) may be powered by one or more power supplies carried by interface appliance 10. For example, the one or more power supplies may include one or both of a battery and/or a capacitor. In this embodiment, electronic interface 30 may not be configured to receive power to interface appliance 10 from an external source.

Figure 2:
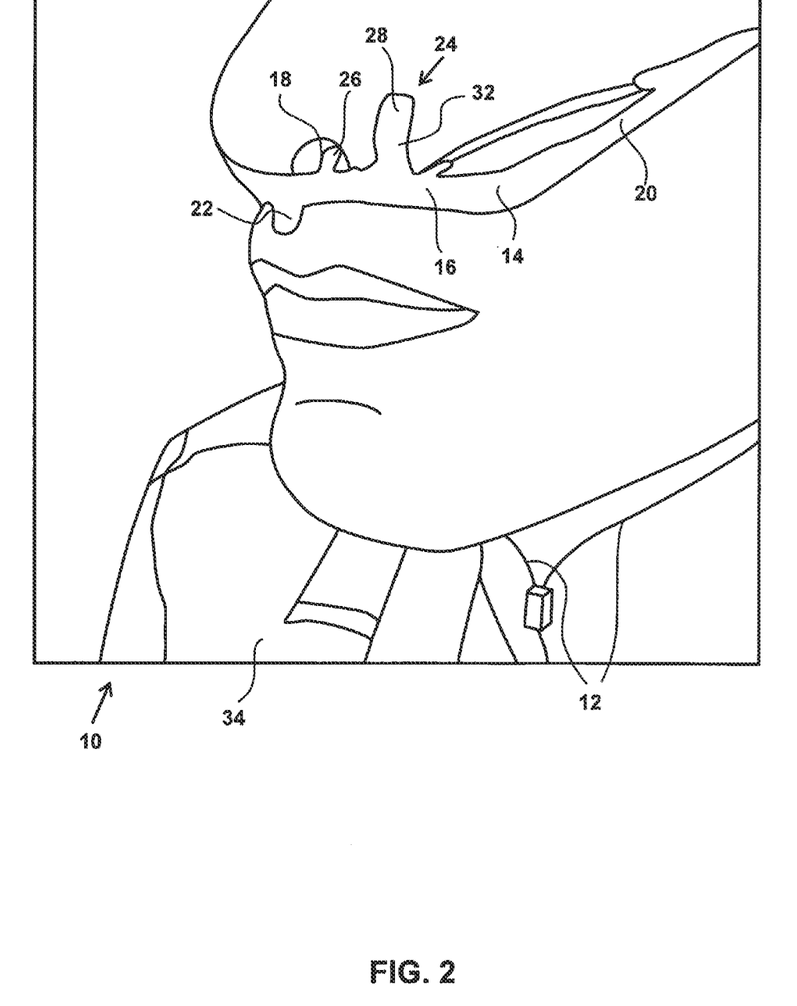
FIG. 2 illustrates an interface appliance configured to deliver a flow of fluid to the airway of a subject, in accordance with one or more embodiments of the invention.

FIG. 2 illustrates interface appliance 10 installed on the face of a subject 34 for use. As can be seen in FIG. 2, if interface appliance 10 is installed on the face of subject 34 with hollow prongs 18 inserted into the nostrils, a portion of pulse oximeter 24 is inserted into the nostrils of subject 34 with hollow prong 18. In the embodiment of interface appliance 10 illustrated in FIG. 2 (and in the embodiment illustrated in FIG. 1), the portion of pulse oximeter 24 inserted into the nostrils of subject 34 with hollow prongs 18 is electromagnetic radiation source 26. This is not intended to be limiting, the relative positions of electromagnetic radiation source 26 and photosensitive detector 28 could be exchanged without departing from the scope of this disclosure.

The electromagnetic radiation source 26 is configured to emit electromagnetic radiation incident on a wall of the nostril of subject 34. The electromagnetic radiation emitted by electromagnetic radiation source 26 includes electromagnetic radiation within the red portion of the visible spectrum ($\lambda$ between about 620 nm and about 750 nm), and electromagnetic radiation within the infrared spectrum ($\lambda$ between about 750 nm and about 100 μm). The electromagnetic radiation source 26 may include one or more of a Light Emitting Diode ("LED"), an Organic Light Emitting Diode ("OLED"), an electroluminescent radiation source ("EL source"), a photoluminescent radiation source ("PL source"), an incandescent source, a laser source, and/or other radiation sources.

The photosensitive detector 28 is carried by nasal cannula 14 such that photosensitive detector 28 receives electromagnetic radiation emitted by electromagnetic radiation source 26 that passes through the nostril wall. The photosensitive detector 28 is configured to generate one or more output signals that convey information related to one or more parameters of the electromagnetic radiation received by photosensitive detector 28. For example, photosensitive detector 28 may be configured to generate output signal(s) that convey information about the intensity of the received electromagnetic radiation within the red portion of the visible spectrum, the intensity of the received electromagnetic radiation within the infrared spectrum, absorbance of electromagnetic radiation within the red portion of the visible spectrum by the wall of the nostril, absorbance of electromagnetic radiation within the infrared spectrum by the wall of the nostril, a difference between the absorbances of electromagnetic radiation within the red portion of the visible spectrum and electromagnetic radiation in the infrared spectrum, and/or other parameters. As will be appreciated, the one or more output signals generated by photosensitive detector 28 can be implemented by a processor to determine the oxygenation of the blood of subject 34 (at least within the nostril wall).

In one embodiment, at least some of the components of interface appliance 10 are re-usable by a given subject, or in some cases, by a plurality of different subjects. In this embodiment, different ones of the components of interface appliance 10 are separable from each other for re-use with new (and/or different) components. This may facilitate a longer lifetime for more expensive components (e.g., one or more of the sensors), and enable cheaper components to be changed out more readily. For example, nasal cannula 14 may be a component that is exchanged by a user relatively frequently due to wear and tear, and/or contamination during typical use. As a result, some or all of pulse oximeter 24 may be usable with different, disposable cannula.

Figure 3:
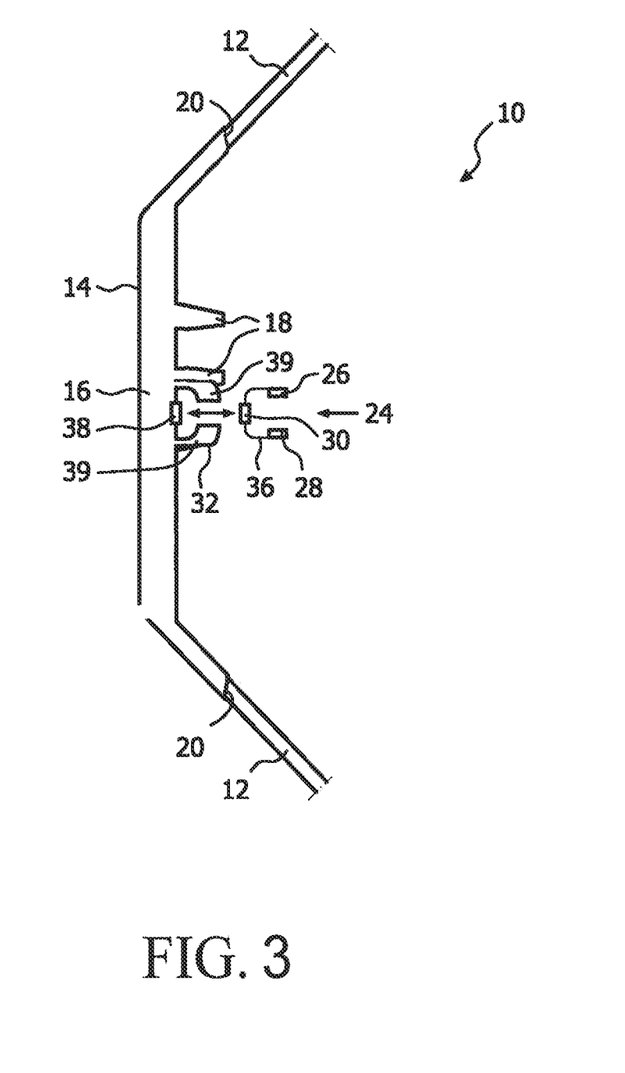
FIG. 3 illustrates an interface appliance configured to deliver a flow of fluid to the airway of a subject, in accordance with one or more embodiments of the invention.

FIG. 3 is an illustration of an embodiment of interface appliance 10 in which pulse oximeter 24 is removable from nasal cannula 14. This enables pulse oximeter 24 to be re-used by a subject (or subjects) with a plurality of different nasal cannula 14. For example, if nasal cannula 14 needs to be exchanged due to wear and tear and/or contamination pulse oximeter 24 can be removed from nasal cannula 14 and installed on another nasal cannula for use by the subject.

As can be seen in FIG. 3, pulse oximeter 24 includes a base 36 that provides a structural base to which the other components of pulse oximeter 24 can be mounted. The base 36 is generally U-shaped, with electromagnetic radiation source 26 being disposed toward one distal end of base 36, and photosensitive detector 28 being disposed toward the other end of base 36. The electromagnetic radiation source 26 and photosensitive detector 28 are disposed on base 36 facing each other. The U-shape of base 36 enables a nostril wall of a subject to be positioned between electromagnetic radiation source 26 and photosensitive detector 28 during use. The electronic interface 30 is disposed on a base 36 such that electronic interface 30 is placed in electronic contact with a corresponding electronic interface 38 on nasal cannula 14 when pulse oximeter 24 is installed on nasal cannula 14. The nasal cannula 14 includes a wiring harness (not shown) for placing electronic interface 38 in electronic communication with an external processor and/or power supply.

To removably hold pulse oximeter 24 in position on nasal cannula 14, one or more of a variety of attachment mechanisms may be employed. For example, pulse oximeter 24 may be removably attached to pulse oximeter 24 via a removable adhesive surface (applied to one or both of pulse oximeter 24 and/or nasal cannula 14), a snap fit (e.g, of base 36 into a corresponding structure on nasal cannula 14), a press fit, a friction fit, a catch, a latch, and/or other mechanisms for releasably attaching components. In one embodiment, nasal cannula forms a pair of sleeves 39 configured to slideably receive the arms of pulse oximeter 24 therein. One of sleeves 39 is formed integrally with one of hollow prong 18. One of sleeves 39 is formed by protrusion 32.

In one embodiment, pulse oximeter 24 is fixedly secured to nasal cannula 14, and the combined device is discarded when it no longer functions and/or becomes unhygienic due to use.

Figure 4:
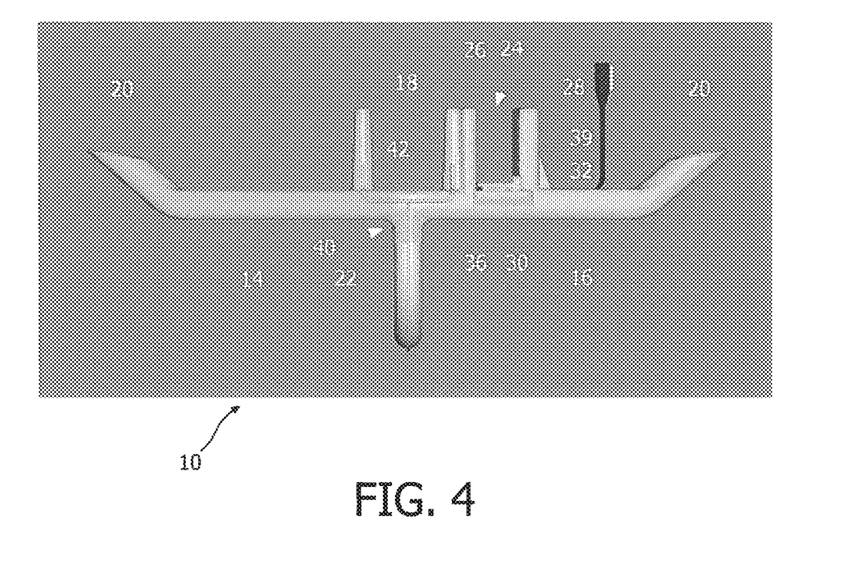
FIG. 4 illustrates an interface appliance configured to deliver a flow of fluid to the airway of a subject, in accordance with one or more embodiments of the invention.

In one embodiment, the one or more sensors carried by nasal cannula 14 include a sensor that generates one or more output signals related to a gas parameter at or near the point of delivery to the subject. By way of illustration, FIG. 4 shows one embodiment of nasal cannula 14 including a sensor 40 disposed, in part, on hollow prongs 18. The sensor 40 is configured to generate one or more output signals related to the flow rate of gas within nasal cannula 14. In particular, sensor 40 includes a thermal sensor 42 that is in thermal communication with the interior of primary conduit 16, hollow prongs 18, and/or a line 44 that extends from interface 22 (e.g., to the mouth of a subject). The thermal sensor 42 may include a thermistor line, a thermocouple and/or other thermal sensors.

As will be appreciated, if thermal sensor 42 is heated with an electrical current, the resistance of thermal sensor 42 will vary as a function of the flow rate of gas through nasal cannula 14. The electrical current is applied to thermal sensor 42 (and monitored for sensing purposes) via the wiring harness of nasal cannula 14. The placement of thermal sensor 42 within nasal cannula 14 at or near the point of interface between interface appliance 10 and the nostrils of the subject (e.g., on hollow prongs 18) may enhance the accuracy of determinations of flow rate at the point of delivery and/or within the airway of the subject.

In one embodiment, not shown in FIG. 4, some or all of sensor 40 may be removable from nasal cannula 14 for re-use. For example, at least a part of thermal sensor 42 may be removed from nasal cannula 14. In one embodiment, sensor 40 may be provided as a sensor that detects flow rate at or near the nostrils of the subject that is provided separately from nasal cannula 14.

Figure 5:
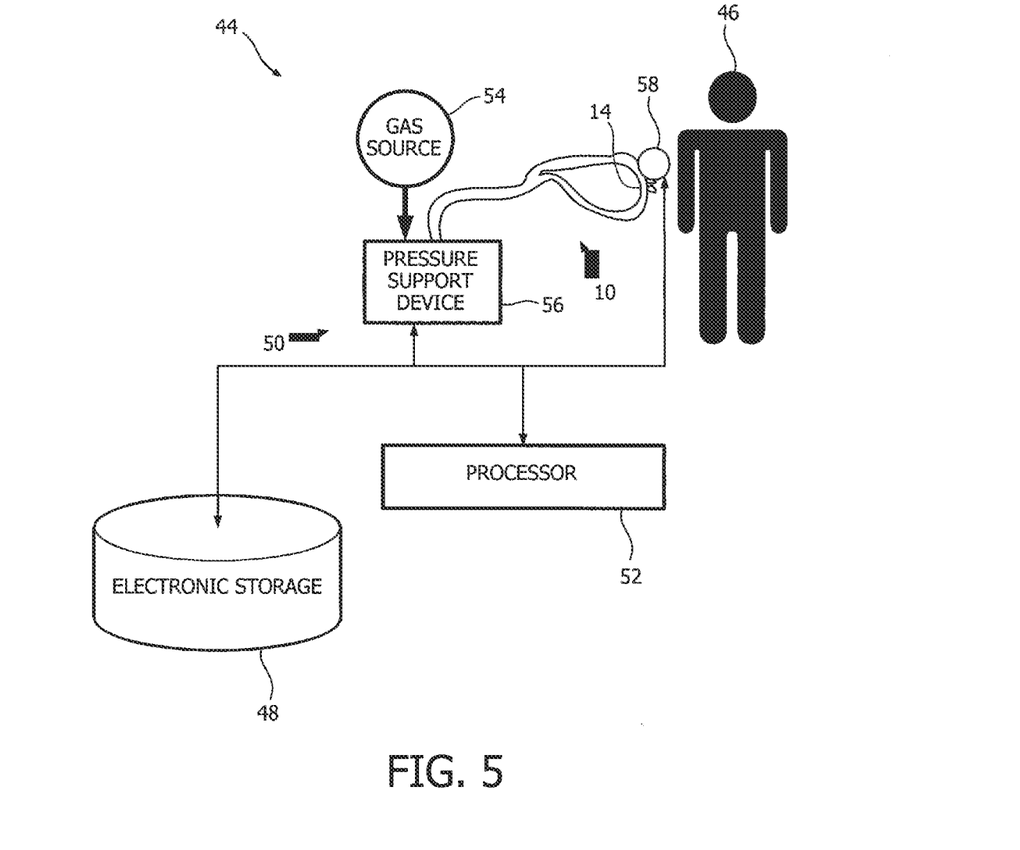
FIG. 5 illustrates an interface appliance configured to deliver a flow of fluid to the airway of a subject, in accordance with one or more embodiments of the invention.

FIG. 5 illustrates a system 44 configured to deliver a flow of fluid to a subject 46. The system 44 may include one or more of interface appliance 10, electronic storage 48, a pressure generator 50, and/or a processor 52.

In one embodiment, electronic storage 48 comprises electronic storage media that electronically stores information. The electronically storage media of electronic storage 48 may include one or both of system storage that is provided integrally (i.e., substantially non-removable) with system 44 and/or removable storage that is removably connectable to system 44 via, for example, a port (e.g., a USB port, a firewire port, etc.) or a drive (e.g., a disk drive, etc.). Electronic storage 48 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 48 may store software algorithms, computer program modules, information determined by processor 52, and/or other information that enables system 44 to function properly. Electronic storage 48 may be a separate component within system 44, and/or electronic storage 48 may be provided integrally with one or more other components of system 44. Although electronic storage 48 is illustrated in FIG. 7 as a single entity, in one embodiment, electronic storage 48 includes a plurality of electronic media divided amongst a plurality of different devices and/or components within system 44.

Pressure generator 50 is configured to generate a flow of fluid for communication to the airway of subject 46 by interface appliance 10. One or more parameters of the flow of fluid may be controlled to provide a therapeutic benefit to subject 46. The one or more parameters of the flow of fluid controlled in accordance with a therapy regime may include one or more of a pressure, a flow rate, a composition (e.g., oxygen content), a volume, and/or other parameters of the flow of fluid. It will be appreciated that in embodiments in which a dual-lumen interface with subject 46 is provided by interface appliance 10, pressure generator not only provides the flow of fluid with a positive pressure, but may include a mechanism that creates a negative pressure within supply lines 12 and/or nasal cannula 14 to convey exhaled gas away from the airway of subject 46. Further, in some embodiments, system 44 may operate to detect one or more parameters without the generation and/or control over the flow of fluid within supply lines 12 and/or nasal cannula. In such embodiments, pressure generators may be turned off, or even omitted entirely from system 44. In one embodiment, pressure generator 50 includes a gas source 54 and a pressure support device 56.

Gas source 54 includes a body or bodies of gas from which pressure support device 56 generates the flow of fluid that is delivered to subject 46. Gas source 54 may include any supply of breathing gas, such as, for example, ambient atmosphere, a tank of pressurized gas, a wall gas source, and/or other bodies of breathable gas. The breathing gas from gas source 56 can be any breathable gas, such as air, oxygen, an oxygen mixture, a mixture of a breathing gas and a medication, which can be in gaseous form (e.g., nitric oxide, nebulized, etc.), and/or other breathable gases.

Pressure support device 56 includes one or more mechanisms for controlling one or more parameters of the flow of fluid released from pressure support device 56 to interface appliance 10 (e.g., pressure, flow, composition, etc.). For example, pressure support device 56 may include one or more of a valve, a blower, a piston, a bellows, and/or other mechanisms for controlling one or more parameters of the flow of breathable gas.

In one embodiment, interface appliance 10 includes one or more sensors 58. The sensors 58 are configured to monitor one or more parameters. For example, sensors 58 may include one or both of the pulse oximeter and/or the flow rate sensor illustrated in FIGS. 2-4 and described above, and/or other sensors.

Processor 52 is configured to provide information processing capabilities in system 44. As such, processor 52 may include one or more of a digital processor, an analog processor, a digital circuit designed to process information, an analog circuit designed to process information, a state machine, and/or other mechanisms for electronically processing information. Processor may be configured to execute one or more computer program modules to provide the functionality discussed below. Although processor 52 is shown in FIG. 5 as a single entity, this is for illustrative purposes only. In some implementations, processor 52 includes a plurality of processing units.

As can be seen in FIG. 5, processor 52 is in operative communication with the sensors 58 to receive the one or more output signals generated by sensors 58. This operative communication may be accomplished via a wireless connection, a wired connection, a network, a dedicated line, and/or other types of communication links.

Processor 52 is configured to control pressure generator 50 in the generation of the flow of fluid for communication to subject 46. This may include controlling pressure generator 50 to adjust one or more gas parameters of the gas in the flow of fluid. The one or more gas parameters may include, for example, pressure, a flow rate, a composition (e.g., oxygen content), a volume, and/or other parameters.

In particular, the processor 52 is configured such that the control of the flow of fluid by processor 52 is based at least in part on the one or more output signals received from sensors 58. The processor 52 may implement the output signals received from energy supply 58 in a feedback manner to control the generation of the flow of fluid, to control a timing of a parameter of the flow of fluid that is cycled with the breathing of subject 46 (e.g., pressure, flow rate, etc.).

By way of non-limiting example, if pressure generator 50 generates the flow of fluid with an elevated level of oxygen, processor 52 may control pressure generator 50 to adjust the level of oxygen in the flow of fluid based on the output signal(s) of sensors 58. In this embodiment, sensors 58 include a pulse oximeter (e.g., as illustrated in FIGS. 2-4 and described above) that generates one or more output signals conveying information related to the oxygenation (oxyhemoglobin saturation) of the blood of subject 46. As such, the output signal(s) provide a feedback upon which control over the level of oxygen in the flow of fluid can be controlled. For instance, if the output signal(s) of sensors 58 indicate that the oxygenation of the blood of subject 46 decreases below a threshold, then the level of oxygen in the flow of fluid is increased. Conversely, if the output signal(s) indicate that the oxygenation of the blood of subject 46 is above a threshold, then the level of oxygen in the flow of fluid is decreased. The threshold(s) may be static, predetermined levels, or may be determined dynamically. In some instances, the level of oxygen in the flow of fluid may be determined according to a function that takes the output signal(s) of sensors 58 (and/or values derived therefrom) as input.

As another example, if the output signal(s) generated by sensors 58 is conveys information related to the flow rate of gas at or near the point of delivery (e.g., as illustrated in FIG. 4 and described above), processor 52 may control pressure generator 50 to adjust the operation of pressure generator 50. For instance, processor 52 may control pressure generator 50 to adjust the pressure and/or flow rate of the flow of fluid at or near pressure generator 50 based on the output signal(s) of sensors 58. This may include, for example, reducing the pressure (e.g., to zero, and/or a negative value) of the flow of fluid during exhalation.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to measure one or more parameters, the system comprising:
   a nasal cannula comprising a main conduit, a pair of sleeves, a protrusion, and a pair of hollow prongs that extend from the main conduit, wherein
      the hollow prongs are configured to be inserted into the nostrils of a subject such that a flow of fluid in the main conduit is communicated to the nostrils of the subject through the hollow prongs,
      the pair of sleeves extend from the main conduit adjacent to the pair of hollow prongs such that a first sleeve is formed integrally with one of the hollow prongs, and a second sleeve is formed by the protrusion, wherein the pair of sleeves, the one of the hollow prongs, and a portion of the main conduit are a monolithic part in the nasal cannula, the protrusion extending away from the main conduit such that during use of the nasal cannula, the first sleeve is inserted in one of the nostrils of the subject and the second sleeve is outside of the one of the nostrils of the subject; and
   a base removably received by the main conduit of the nasal cannula, the base comprising:
      one or more sensors disposed on the base such that at least a portion of the one or more sensors is disposed on or directly adjacent to at least one of the hollow prongs, the one or more sensors being configured to generate one or more output signals that convey information related to at least one parameter related to the flow of fluid between the nostrils of the subject and the nasal cannula;
      wherein the at least one parameter is associated with pulse oximetry, and wherein the one or more sensors comprise a pulse oximeter, the pulse oximeter comprising:
         an electromagnetic radiation source configured to emit electromagnetic radiation incident on a wall of one of the nostrils of the subject responsive to the hollow prongs being inserted into the nostrils of the subject; and a photosensitive detector configured to receive a portion of the electromagnetic radiation emitted by the electromagnetic radiation source that propagates through the wall of the nostril; wherein the electromagnetic radiation source and the photosensitive detector are configured to be positioned on an inner nostril wall and an outer nostril wall located on the exterior surface of the nose of the subject during use of the nasal cannula; and a first electronic interface disposed on a coupling portion of the base in electronic contact with a corresponding second electronic interface disposed on the nasal cannula between the pair of sleeves, wherein the one or more output signals generated by the one or more sensors are output via the first electronic interface.

2. The system of claim 1, further comprising: a pressure generator configured to generate a flow of fluid; and wherein a processor is configured to control the pressure generator such that one or more gas parameters of the gas in the flow of fluid is controlled in a feedback manner based on the one or more output signals of the one or more sensors.

3. The system of claim 1, wherein the at least one parameter further comprises the flow rate within the nasal cannula.

4. The system of claim 1, wherein the base is removable from the nasal cannula such that the base can be reused with another nasal cannula.

5. The system of claim 1, wherein the base is generally U-shaped including a first distal end, and a second distal end, such that the first distal end is in contact with the first sleeve and the second distal end is in contact with the second sleeve, and wherein the first electronic interface is disposed on the coupling portion of the base.

6. The system of claim 1, wherein the at least one parameter further comprises one or more physiological parameters of the subject.

7. The system of claim 6, wherein the first electronic interface includes one or more wireless transmitters and or receivers to communicate the output signals wirelessly.

8. A method of determining a parameter with a nasal cannula comprising a main conduit; a pair of hollow prongs configured to be inserted into the nostrils of a subject; a protrusion; and a pair of sleeves extending from the main conduit such that a first sleeve is formed integrally with one of the hollow prongs, and a second sleeve is formed by the protrusion, wherein the pair of sleeves, the one of the hollow prongs, and a portion of the main conduit are a monolithic part in the nasal cannula, the protrusion extending away from the main conduit such that during use of the nasal cannula, the first sleeve is inserted in one of the nostrils of the subject a protrusion and the second sleeve is outside of the one of the nostrils, the method comprising:

communicating a flow of fluid with the nostrils of the subject through the nasal cannula;

generating one or more output signals that convey information related to at least one parameter related to the flow of fluid between the nostrils of the subject and the nasal cannula, wherein the one or more output signals are generated by one or more sensors disposed on a base such that at least a portion of the one or more sensors is disposed on or directly adjacent to at least one of the hollow prongs;

wherein the at least one parameter is associated with pulse oximetry, and wherein generating one or more output signals that convey information related to the at least one parameter comprises:

emitting electromagnetic radiation onto a wall of one of the nostrils of the subject;

receiving a portion of the electromagnetic radiation emitted by the electromagnetic radiation source that propagates through the wall of the nostril; and generating an output signal that conveys information related to one or more radiation parameters of the received electromagnetic radiation; wherein the electromagnetic radiation source and the photosensitive detector are configured to be positioned on an inner nostril wall and an outer nostril wall located on the exterior surface of the nose of the subject during use of the nasal cannula; and communicating the one or more output signals generated by the one or more sensors via a first electronic interface disposed on the base, wherein the first electronic interface is in electronic contact with a corresponding second electronic interface disposed on the nasal cannula between.

9. The method of claim 8, further comprising:
generating the flow of fluid; and
controlling one or more aspects of the generation of the flow of fluid in a feedback manner based on the one or more output signals of the one or more sensors.

10. The method of claim 8, wherein the at least one parameter further comprises the flow rate of gas within the nasal cannula.

11. The method of claim 8, wherein the base is removable from the nasal cannula such that the base can be reused with another nasal cannula.

12. The method of claim 8, wherein the base is generally U-shaped including a first distal end, a second distal end, and a coupling portion such that the first distal end is in contact with the first sleeve and the second distal end is in contact with the second sleeve, and wherein the first electronic interface is disposed on the coupling portion of the base.

13. The method of claim 8, wherein the at least one parameter further comprises one or more physiological parameters of the subject.

14. The method of claim 13, further comprising wirelessly communicating the output signals generated by the one or more sensors via the first electronic interface wherein the first electronic interface includes one or more wireless transmitters and or receivers.

15. A system configured to determine a parameter, the system comprising:

means for communicating a flow of fluid with the nostrils of a subject, the means for communicating the flow comprising a main conduit; a pair of hollow prongs configured to be inserted into the nostrils of a subject; a protrusion; and a pair of sleeves extending from the main conduit such that a first sleeve is formed integrally with one of the hollow prongs, and a second sleeve is formed by the protrusion, wherein the pair of sleeves, the one of the hollow prongs, and a portion of the main conduit are a monolithic part in the nasal cannula, the protrusion extending away from the main conduit such that during use of the means for communicating, the first sleeve is inserted in one of the nostrils of the subject and the second sleeve is outside of the one of the nostrils;

means for generating one or more output signals that convey information related to at least one subject parameter related to the flow of fluid between the nostrils of the subject and the means for communicating, wherein the means for generating the one or more output signals are disposed on a base removably received by the main conduit of the means for communicating the flow at least a portion of the means for generating the one or more output signals is disposed on or directly adjacent to at least one of the hollow prongs;

wherein the at least one parameter is associated with pulse oximetry, and wherein the means for generating one or more output signals that convey information related to the at least one subject parameter comprise:

means for emitting electromagnetic radiation onto a wall of one of the nostrils of the subject;

means for receiving a portion of the electromagnetic radiation emitted by the means for emitting electromagnetic radiation that propagates through the wall; wherein the means for emitting electromagnetic radiation and the means for receiving the portion of the electromagnetic radiation are configured to be positioned on an inner nostril wall and an outer nostril wall located on the exterior surface of the nose of the subject during use of the means for generating; and first means for communicating the one or more output signals generated by the means for generating, wherein the first means for communicating are disposed on the base, and wherein the first means for communicating are in electronic contact with a corresponding second means for communicating disposed on the means for communicating flow between the pair of sleeves on the means for communicating the flow.

16. The system of claim 15, further comprising:
means for generating the flow of fluid; and
means for controlling the means for generating the flow of fluid in a feedback manner based on the one or more output signals.

17. The system of claim 15, wherein the at least one parameter further comprises the flow rate within the upper airway of the subject.

18. The system of claim 15, wherein the base is removable from the means for communicating such that the base can be reused with means for delivering.

19. The system of claim 15, wherein the base is generally U-shaped including a first distal end, a second distal end, and a coupling portion such that the first distal end is in contact with the first sleeve and the second distal end is in contact with the second sleeve, and wherein the first means for communicating is disposed on the coupling portion of the base.

20. The system of claim 15, wherein the at least one parameter further comprises one or more physiological parameters.

21. The system of claim 20, wherein the first means for communicating the output signals include one or more wireless transmitters and receivers, and wherein the first means are configured to wirelessly communicate the output signals generated by the means for generating one or more output signals.

* * * * *